United States Patent
Cascioli (12) 
(10) Patent No.: US 11,062,591 B1
(45) Date of Patent: Jul. 13, 2021

(54) SYSTEMS AND METHODS FOR GENERATING DEVICE-AGNOSTIC DATA AND A TRAINING DASHBOARD FROM WEARABLE AND NON-WEARABLE DEVICES

(71) Applicant: ARCHITECTURE TECHNOLOGY CORPORATION, Eden Prairie, MN (US)

(72) Inventor: Joseph Cascioli, Ithaca, NY (US)

(73) Assignee: Architecture Technology Corporation, Eden Prairie, MN (US)

(*) Notice: Subject to any disclaimer, the term of this patent is extended or adjusted under 35 U.S.C. 154(b) by 138 days.

(21) Appl. No.: 16/268,371

(22) Filed: Feb. 5, 2019

(51) Int. Cl.
| | |
|---|---|
| G08B 25/01 | (2006.01) |
| G16H 50/30 | (2018.01) |
| G16H 10/60 | (2018.01) |
| G08B 21/04 | (2006.01) |
| G08B 25/10 | (2006.01) |
| G06F 9/54 | (2006.01) |
| G06F 16/21 | (2019.01) |
| G06F 1/16 | (2006.01) |

(52) U.S. Cl.
CPC .......... *G08B 25/016* (2013.01); *G06F 9/547* (2013.01); *G08B 21/0453* (2013.01); *G08B 25/10* (2013.01); *G16H 10/60* (2018.01); *G16H 50/30* (2018.01); *G06F 1/163* (2013.01); *G06F 16/21* (2019.01)

(58) Field of Classification Search
CPC .. G08B 25/10; G08B 25/016; G08B 21/0453; G16H 50/30; G06F 9/547; G06F 16/21; G06F 1/163

USPC ..................................................... 340/539.11
See application file for complete search history.

(56) References Cited

U.S. PATENT DOCUMENTS

| | | | | |
|---|---|---|---|---|
| 5,946,605 | A * | 8/1999 | Takahisa ................. | H04H 20/28 |
| | | | | 455/150.1 |
| 2013/0080114 | A1* | 3/2013 | Stergiou .................... | G06N 5/02 |
| | | | | 702/176 |
| 2016/0063873 | A1* | 3/2016 | Zimmer .................. | G06Q 50/20 |
| | | | | 434/353 |
| 2016/0275781 | A1* | 9/2016 | Nold ....................... | G08B 13/08 |
| 2016/0330182 | A1* | 11/2016 | Jeon ....................... | H04L 63/062 |
| 2018/0064401 | A1* | 3/2018 | Nathan .................. | G16H 40/67 |

OTHER PUBLICATIONS

Joseph Cascioli, Phase I SBIR Proposal, "ABBET—Army Basic Blended Training", Topic No. and Name: A18-030—Data tools for the Army Basic Training Environment, Feb. 7, 2018, 24 pages.

* cited by examiner

*Primary Examiner* — Quan-Zhen Wang
*Assistant Examiner* — Mancil Littlejohn, Jr.
(74) *Attorney, Agent, or Firm* — Foley & Lardner LLP (57) ABSTRACT

Disclosed herein are systems and methods for receiving electronic healthcare records and wearable device data associated with multiple users from multiple data sources, which are configured to generate and store the data in various data model regimes, many of which are not standardized or are variants of a standard. The data is standardized, aggregated, and then analyzed to generate reports. The reports are used to provide a plurality of customized execution environments and user interfaces on computing devices of the users, based on a report of each user. The data is used to determine distress situations and provide alert notifications in response.

20 Claims, 6 Drawing Sheets

```
"actor": {
    "name": "Jane Doe",
    "mbox": "555-55-5555"
},
"verb": {
    "id": "http://adlnet.gov/expapi/verbs/completed",
    "display": { "en-US": "completed" }
},
"object": {
    "id": "http://example.com/activities/basic-training-week-one",
    "definition": {
        "type": "http://adlnet.gov/expapi/activities/course",
        "name": { "en-US": "Week One" }
    }
},
"context": {
    "instructor": {
        "name": "John Instructor",
        "mbox": "mailto:john@example.com"
    }
},
"result": {
    "completion": true,
    "success": true,
    "extensions": {
        "http://example.com/bio/average-active-heart-rate": 75
    }
}
```

SYSTEMS AND METHODS FOR GENERATING DEVICE-AGNOSTIC DATA AND A TRAINING DASHBOARD FROM WEARABLE AND NON-WEARABLE DEVICES

TECHNICAL FIELD

This application relates generally to transformation of data from multiple types of wearable and non-wearable devices to a device agnostic dataset and generating a training dashboard based on the device agnostic dataset.

BACKGROUND

Miniaturization in electronic technology has led to an explosion of small electronic devices, especially in the recent decades. For example, system on a chip (SoC) technology has allowed electronic device manufacturers to produce highly complex and programmable sensors in very small form factors. A wrist worn smartwatch available now may have as much processing power, memory, and storage as a desktop computer available a decade ago. These small electronic devices are ubiquitous in this day and age, the prime examples being smartphones, fitness trackers, and smartwatches.

A combination of the miniaturization and consumer interest in personal health has led to a variety of wearable devices (e.g., personal fitness devices and trackers) being offered on the market. Such wearable are typically designed for use with a single activity, e.g., physical activity. The wearable have enabled many users to change their lifestyles for the better, and have become increasingly popular over the years. For instance, the wearable assist each user in providing feedback, goal setting, and behavior change strategies, which can be effective when altering exercising habits of the user.

A major problem with the wearable devices is that they are provided by different manufacturers and generate data in different formats. These formats are may not be compatible with each other. Furthermore, the data format of the wearable devices may not be compatible with the data format of non-wearable electronic devices such as electronic sensors. This lack of compatibility severely restricts monitoring users as a group and generating automated feedback based upon one or more group attributes.

SUMMARY

What is therefore desired are methods and systems for receiving data in a plurality of formats from both wearable and non-wearable devices and transforming the data into a device agnostic inter-compatible format. What is further desired are systems and methods that generate a training dashboard for a group of users based on the device agnostic data and provide feedback to the group of users based upon one or more group attributes.

A method and a system disclosed herein may execute instructions to generate an experience application programming interface (xAPI), which may collect fitness training data and healthcare data associated with multiple users from multiple devices and applications, and then standardize collected data. The xAPI may provide a blended training environment for each group of multiple users, which tracks each user's data, collect each user's data, and then aggregates each user's data with data associated with other users to analyze and correlate the experiences of each user in the group. The fitness training data and the healthcare data of each user may include, but not limited to, heart rate information obtained multiple sensors, medical records obtained from a healthcare application on a user mobile device, information from an electronic target that recorded user's shots on a training field, and manually inputted information in the healthcare application such as user's psychological responses for stress, fear, or confidence. The aggregated data associated with the multiple users may be used to determine multiple correlations between the aggregated data that were not possible to obtain with the raw training data and healthcare data associated with a single user. Analysis of the aggregated fitness training data and healthcare data is made deliverable in reports, visualized in graphs, and viewed remotely by each user accessing a dashboard of their user computing device.

In an embodiment, a computer implemented method comprises continuously receiving, by a computer, body-worn sensor data from body-worn sensors of a plurality of users, non-body-worn sensor data associated with the plurality of users and collected from non-body-worn sensors; converting, by the computer, the body-worn sensor data and the non-body-worn sensor data into device-agnostic experience application programming interface (xAPI) data format; determining, by the computer, a distress situation of a user of the plurality of users based upon non-body-worn sensor data retrieved between a first timestamp and a second timestamp; correlating, by the computer, the non-body-worn sensor data between the first timestamp and the second timestamp to body-worn sensor data of the user between the first timestamp and the second timestamp; determining, by the computer, whether the body-worn sensor data of the user between the first timestamp and the second timestamp indicates a distress situation; and in response to the computer determining the distress situation from the non-body sensor data and the body-worn sensor data: transmitting, by the computer, a distress alert notification to a second user of the plurality of users.

In another embodiment, a computer-implemented method comprises. continuously receiving, by a computer, body-worn sensor data from body-worn sensors of a plurality of users, non-body-worn sensor data associated with the plurality of users and collected from non-body-worn sensors; converting, by the computer, the body-worn sensor data and the non-body-worn sensor data into device-agnostic experience application programming interface (xAPI) data format; determining, by the computer, a distress trigger situation of a user of the plurality of users based upon non-body-worn sensor data retrieved between a first timestamp and a second timestamp; correlating, by the computer, the non-body-worn sensor data between the first timestamp and the second timestamp to the body-worn sensor data of the user between the first timestamp and the second timestamp; determining, by the computer, whether the body-worn sensor data of the user between the first timestamp and the second timestamp indicates a distress situation; and in response to the computer determining a distress situation based upon the body-worn sensor data: transmitting, by the computer, a distress alert notification to a second user of the plurality of users.

In yet another embodiment, a system comprises a non-transitory storage medium storing a plurality of computer program instructions; a processor electrically coupled to the non-transitory storage medium and configured to execute the plurality of computer program instructions to: continuously receive body-worn sensor data from body-worn sensors of a plurality of users, non-body-worn sensor data associated with the plurality of users and collected from non-body-worn sensors; convert the body-worn sensor data and the non-body-worn sensor data into device-agnostic experience application programming interface (xAPI) data format; determine a distress situation of a user of the plurality of users based upon non-body-worn sensor data retrieved between a first timestamp and a second timestamp; correlate the non-body-worn sensor data between the first timestamp and the second timestamp to the body-worn sensor data of the user between the first timestamp and the second timestamp; determine whether the body-worn sensor data of the user between the first timestamp and the second timestamp indicates a distress situation; and in response to the processor determining the distress situation from the non-body sensor data and the body-worn sensor data: transmit a distress alert notification to a second user of the plurality of users.

BRIEF DESCRIPTION OF THE DRAWINGS

The accompanying drawings constitute a part of this specification and illustrate embodiments of the subject matter disclosed herein.

DETAILED DESCRIPTION

Reference will now be made to the illustrative embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one ordinarily skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Disclosed herein is a system that aggregates many forms of fitness training data and healthcare data collected from various fitness trackers, sensors, and healthcare devices operated by a group of users. The system may execute machine learning algorithms on the aggregated data to analyze the data. The machine learning algorithms may use predictive analytics to analyze of the data and predict future training outcomes for the users. Based on the results of the analysis, the system may enable the group of users to track their fitness goals, keep the group of users engaged and informed about their data records, and determine correlations between the different types of data associated with the group of users. Prior to the analysis, the system may standardize the collected fitness training data and the healthcare data into one single format to allow for easier processing of the collected data, and to extend the system into coupling with any fitness device of the user. The configuration of the system may create a secure blended learning environment, which may accurately explain how each user trains and learns. For example, if a user from the group of users is going through a fitness training program, and a heartrate or other healthcare data of the user correlate to a failing fitness test score, an alert may be generated. The alert may be transmitted to an analyst computer. The analyst computer may process information associated with the alert to determine recommended learning material for the user associated with the alert. The analyst computer may transmit the recommended additional learning material to a user computing device of the user. The recommended learning material is displayed on a graphical user interface of the user computing device.

A server computer of the system may generate and customize an experience application programming interface (xAPI) to provide a blended training environment for users. The xAPI is device agnostic and portable, which enables the xAPI to be used with all types of fitness tracking devices. The xAPI may track user's training data on the fitness tracking devices. The xAPI may standardize the tracked data. The xAPI may aggregate the standardized data with data of other users to analyze and correlate experiences of the users. The xAPI may receive the data from many data sources such as fitness tracking devices and/or healthcare applications associated with the fitness tracking device. For example, heart rate data from fitness trackers, information associated with an electronic target that recorded the user's shots on a field, and manually entered information such as the user's psychological responses. The xAPI may use different kinds of the data to find various correlations between attributes associated with the data. All the data is then made deliverable in form of reports on a dashboard GUI of a user computing device where the reports may be visualized in graphs.

The xAPI is able to provide a blended training environment by aggregating fitness data as well as learning data of the users. Using the fitness data and the learning data, the xAPI correlate different information from heart rate, to amount of sleep the user got, the food the user ate, to if the user read training material prior to a physical activity. The blended training for the users is important because it better records how an individual user actually learns. The xAPI may also provide the users not only with metrics on their training, but also with training material about upcoming courses, advice on improving their current scores, and standard learning material. An analyst may execute the xAPI on analyst computer to craft and implement interventions, such as fitness goals for the users to keep the users improving throughout their training.

The server computer may also determine distress situations and generate alert notification in response. For example, based upon sensor data received from a car, the server computer may determine that a car may have been involved in accident (e.g., indicated by a rapid deceleration or hard braking). The server computer may confirm the distress situation by analyzing body-worn sensor data in the same time-frame. For example, for users in the car, the body-worn sensor data may indicate spike in heart rate or a sudden movement. When the server computer determines the distress situation, the sever computer may generate and transmit alert to other users and/or authorities.

In some embodiments, the server computer may determine a distress trigger situation based upon sensor data received from non-body-worn sensors, e.g., a window sensor in a home indicating whether the window is open or closed. When the window sensor indicates that the state of the window as changed from closed to open, the server computer may flag a distress trigger. The opening of the window may be associated with a home invasion. The server computer may analyze the data generated by bod-worn sensors of users inside the home. If the body-worn sensors indicate distress (e.g., spiked heart rate, sudden movements), the server computer may determine a distress situation and generate alert notifications. If the body-worn sensors do not indicate a distress, the server computer may indicate a false alarm.

Figure 1:
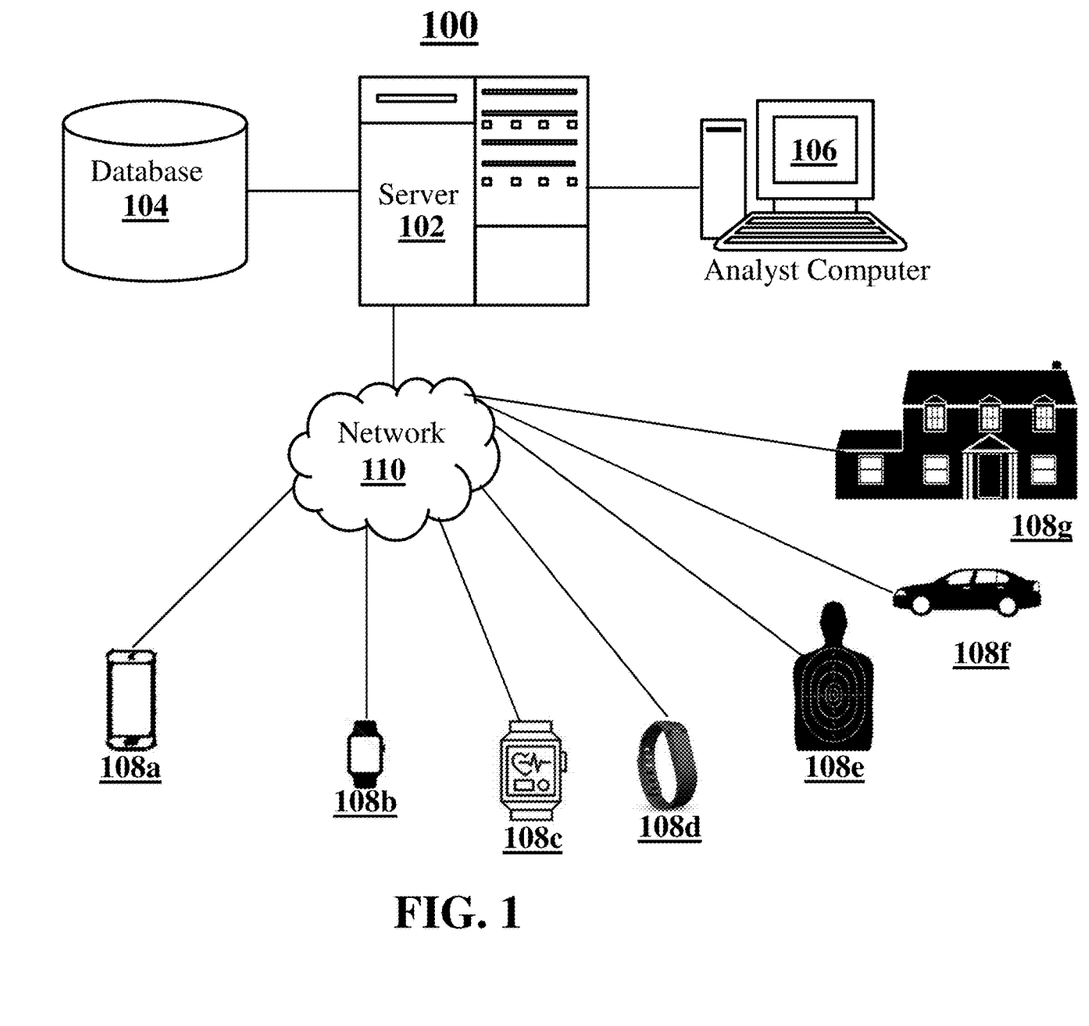
FIG. 1 illustrates a system for processing fitness training data and healthcare data, according to an embodiment.

FIG. 1 illustrates a system 100. The system 100 may include a server 102, a database 104, an analyst computer 106, sensors 108a-108g (collectively and commonly referred to as 108), and a network 110. The server 102, the database 104, the analyst computer 106, the sensors 108, and the network 110 may be connected to each other through a network 110. The examples of the network 110 may include, but are not limited to, private or public LAN, WLAN, MAN, WAN, and the Internet. The network 110 may include both wired and wireless communications according to one or more standards and/or via one or more transport mediums. The communication over the network 110 may be performed in accordance with various communication protocols such as Transmission Control Protocol and Internet Protocol (TCP/IP), User Datagram Protocol (UDP), and IEEE communication protocols. In one example, the network 110 may include wireless communications according to Bluetooth specification sets, or another standard or proprietary wireless communication protocol. In another example, the network 110 may also include communications over a cellular network, including, e.g. a GSM (Global System for Mobile Communications), CDMA (Code Division Multiple Access), EDGE (Enhanced Data for Global Evolution) network.

In operation, a server 102 may execute an experience application programming interface (xAPI) to collect sensor data from a variety of data sources such as sensors 108 and applications of multiple users in a group over a network 110. The server 102 may then standardize the data according to a common data model. The server 102 may then store standardized data in a database 104. The server 102 may execute analytical algorithms on the standardized data to correlate various attributes associated with the data. The server 102 may generate reports and insights based on the results of the correlation between the attributes associated with the data. In some cases, the server 102 may transmit the standardized data to an analyst computer 106 over the network 110. The analyst computer 106 may process the standardized data by executing the analytical algorithms on the standardized data. Based on the processing, the analyst computer 106 may generate the reports and the insights. The analyst computer 106 may display the data reports and the insights through various interactive graphical user interfaces to an end user device, in accordance with a particular function or an application executed by the analyst computer 106.

Sensors 108 may be computing devices comprising a processor and capable of performing various tasks and processes described herein. Non-limiting examples of the sensors 108 may include a user mobile device 108a having a healthcare application, a first smartwatch 108b having a healthcare application, a second smartwatch 108c having a healthcare application, a fitness tracker 108d having, an electronic target 108e, a car sensor 108f, and a home sensor 108g.

The sensors 108 may be embedded or associated sensors, such as, motion sensors, thermal sensors, weight sensors, and camera sensors, which may act as a data source for a processor to supplement data, as generated by various sensors 108 physically associated with the processor. The sensors may provide opportunities for users operating the devices containing the sensors to experiment with diet, exercise, and lifestyle to optimize key indicators of health.

The sensors 108 may generate sensor data. For examples, sensors 108a (within a smartphone) 108b (within a smartwatch), 108c (within an exercise watch), 108d (within a fitness tracker) may continuously monitor a user's movement and/or vital data. For instance, an accelerometer may track the user's movements and a global positioning system (GPS) sensor may sensor may track the user's location. Sensor 108e may be integrated within an electronic target device may track a user's shot. Sensors 108f may be sensors within a car such as acceleration sensor continuously monitoring the acceleration/deceleration of the car. Sensors 108f may further be airbag sensors monitoring whether corresponding airbags have been deployed. Sensors 108f may also be braking sensors that may detect braking patterns of the user. Sensors 108g may be home sensors such as window/door sensors and smart doorbells. For example, a sensor 108a may track the openings and closings of doors and windows in a home. A smart doorbell may track when someone approaches and/or presses a doorbell button.

A server 102 may a computing device comprising a processor and non-transitory machine-readable storage medium, and capable of performing the various tasks and processes described herein. Non-limiting examples of the server 102 may include a desktop computer, a server computer, a laptop computer, a tablet computer, or the like. For ease of explanation, FIG. 1 shows a single computing device functioning as the server 102. However, it should be appreciated that some embodiments may comprise any number of computing devices functioning as the server 102 capable of performing the various tasks described herein.

The server 102 may be directly or indirectly associated with sensors 108 of multiple users. The server 102 may be directly or indirectly associated with healthcare applications associated with the sensors 108. The server 102 may periodically receive the sensor data from the sensors 108 and/or the healthcare applications. The sensor data may include fitness training data and healthcare data such as sleep pattern data, step data, running data, swimming data, heart rate data, weight data, and images of user doing various exercises. The server 102 may periodically transmit a request to the sensors 108 and/or the healthcare applications to receive the fitness training data and the healthcare data. Upon receiving the request, the sensors 108 and/or the healthcare applications may transmit the fitness training data and the healthcare data to the server 102. In some cases, the sensors 108 and/or the healthcare applications may on its own transmit the fitness training data and the healthcare data to the server 102 after a predetermined interval of time. The records of the fitness training data and the healthcare data may include information from a user mobile device having a healthcare application, information from a first smartwatch, information from a second smartwatch, information from a third smartwatch, information from an electronic target that recorded user's shots on a training field, information about operation of a car, and information about states in a home The server 102 may format and organize the records of sensor data of the multiple users into a group record for each group of users. The server 102 may generate a group profile record for each group of users that is compiled using the incoming data records received from various data sources. Prior to grouping the data, on receiving the sensor data from the sensors 108 and the applications, the server 102 may convert the arriving data into standardized data. The server 102 may execute a standardized data model on the fitness training data and the healthcare data to generate the standardized data.

For example, the server 102 may convert the inbound fitness training data and the healthcare data received from multiple source data models associated with the sensors 108 to a standardized model employed by various components of a fitness data service being executed by the server 102. To convert the incoming data records, the server 102 may map various data fields of the inbound data records to the data fields of the standardized data model. For instance, the data records arriving from the sensors 108 may provide inbound records having a first data model. The server 102 may then convert the inbound records to the standardized model, associated with a group identifier and store into the database 104. In one example, the data records may be integrated with universal fitness care concept codes of the standardized model to allow the data records to be encoded under specific medical diagnostic concepts. In some cases, the server 102 may capture, share, and aggregate the data records collected from the variety of sensors 108 in a consistent manner by the standardized model universal fitness care concept codes terminology. The terminology may contain hierarchically specified fitness care concepts, each with unique meanings and logic-based definitions. Additionally, the fitness care concepts may have distinct relationships that support reliability and consistency for fitness data record retrieval from the variety of data sources. As used herein, the universal fitness care concept codes corresponds to a standardized data model language that enables a consistent way of indexing, storing, retrieving, formatting, and aggregating fitness data record across specialties and sites of medical care obtained from the variety of data sources. Each universal fitness care concept code is a unique identifier indicative of a node in a hierarchy of fitness care concepts to which other types of fitness data record obtained from the variety of data sources can be mapped.

The server 102 may be coupled to the sensors 108 via networks 110. The server 102 may execute various processes on incoming data records received from the sensors 108, such as data field formatting or identifying an associated group user, and then generating the group record. Each group record corresponds to a form such as a healthcare form or application, and contains various fields that are associated with instances of the form or application. The server 102 initially populate the group record form with information provided from the users, information collected from the sensors 108 or another source. After the group record is initially populated, the server 102 assigns status values to the fields in the group record. The server 102 may execute instructions to indicate a status of fields in the group record stored in the database 104. In some cases, the server 102 automatically assigns a status to each field in the group record. To automatically assign status values to fields in the group record, the server 102 compares the data stored in each field to other data associated with the user. Referring to record context, for instance, certain fields in the group record may be populated for every user including data collected from the sensors 108 and/or the healthcare applications. In some cases, the format of the data provided in each field may be defined, for instance, body weight field should include a kilograms. A set of rules reflecting the format may be obtained by the server 102 from the database 104. The server 102 in turn can automatically assign status values to fields in the group record based on the rules, for instance, assigning a value of missing data to any field where data is expected and is not there, a status of incorrect data to any field where the data provided does not conform to an expected value, a status of incomplete data where data entered is only partial, or by any other status that could be predefined by the server 102.

In operation, the server 102 may execute software modules (e.g., APIs, web hooks, and web sprockets) to consume (e.g., retrieve/pull, receive), from various sensors 108 and/or the healthcare applications, inbound data records that may then be parsed and reconstructed into a standardized data model format. The interface software modules may receive or pull data from particular sensors 108 and/or the healthcare applications, as required by the particular sensor 108 and/or the healthcare application. In some cases, the sensor 108 and/or the healthcare application may transmit a set of records at regular interval, using a data transfer protocol (e.g. FTP, SFTP). Using inbound data records received from the various sensors 108 and/or the healthcare applications, the software modules executed by the server 102 may generate database records for the database 104. Data models may define the data fields of inbound records and/or the data fields of the standardized data model, allowing the server 102 to map incoming data models to the standardized data model. In some implementations, an inbound interface software module of the server 102 may compare certain fields of two inbound data records arriving from disparate sensors 108 and/or the healthcare applications, to determine whether the two inbound records are related to users in a same group. The server 102 may determine whether a new inbound record is related to the users of an existing group record previously stored in a database 104. The server 102 may execute analytics algorithms on the inbound data records that may cross-reference data, correlate data, and/or perform metrics calculations, using the inbound data records stored in the databases 104.

The databases 104 may store the inbound data records comprising data fields that are associated with particular groups of users. The server 102 may parse certain data fields of the inbound data records into distinct records or fields of data records of the database 104 in accordance with the standardized model, as indicated by the execution of the API. It should be appreciated that, although the system 100 shows only one database 104, however the system 100 may comprise any number of databases 104, hosted on any number computing devices, which may be any computing device comprising a non-transitory machine-readable storage medium and capable of performing the various tasks described herein.

The server 102 may execute AI models on the group record to determine whether a data gap is present within the group record. The AI models may be computer files stored on the server 102 or a separate database device, such as the database 104, and comprise a set of attributes that indicate a type of potential data gap. Upon the execution of the AI models, the server 102 may identify data field entries in the group record that matches to corresponding attributes in the AI models. In one example, the server 102 upon processing the incoming data records of the user may identify a data gap where the user running data is missing for a couple of days. In such a case, the server 102 may generate a flag for data gap associated with the incomplete running data.

The server 102 may store information associated with the data gap in the database 104. The server 102 may use the data gap information to determine what follow up actions need to be taken. The server 102 may generate an alert upon identifying the data gap. The server 102 may determine how to obtain the required data or generate requests for confirmations of the missing data from the sensors 108 and/or the healthcare applications. In some cases, another server of a centrally hosted the system 100 receives a notification of status information from the server 102 specifying the data gap and how the missing information should be recovered. The notification may indicate that several different sensors 108 and/or the healthcare applications need to be queried for missing information, for instance, if the information resides in different places. The server 102 may issue requests to all the different sources of data, such as different sensors 108 and/or the healthcare applications, and thereby minimizing the hassle for the users to provide the missing data.

The server 109 may query different sensors 108 and/or the healthcare applications in response to indication of the missing data, and retrieves information about missing records that require follow up action. The server 102 may generate a request, and transmit the request to the user mobile device 108a, based on instructions from the user, stored in the database 104. The server 102 may solicit the missing data electronically. The request may be automatically formulated, or may be created and provided to the user mobile device 108a through an interface for verification before sending. The request may include a web link to a secure webpage or a data object that can be populated, saved, and returned to the server 102. For example, the webpage contains the missing data fields and spaces to fill in the missing data. The webpage may be provided with options for communicating with the server 102. The webpage may further include various links to information about the requested missing data, and an option to provide a comment for any of the missing data fields.

If the user mobile device does not respond within a predetermined period of time or a response is incomplete or prompts further inquiry, a reminder or follow-up request may be provided to the user mobile device. Once the correct and accurate data for missing field has been supplied by the user mobile device, the server 102 may remove any missing data tag from the group record, and update the group record with information provided by the user mobile device in response to the request for missing data, and store the updated group record in the database 104. The server 102 may perform additional calculations or assessments based on information stored in the updated group record stored in the database 111. Once the group record of the users is complete and accurate, the server 102 may apply one or more analytical models and/or algorithms on the group record stored in the database 102 to calculate reports and insights for the multiple users. In some cases, the server 102 may output the record to the analyst computer 106 for further processing. The analyst computer 106 may apply one or more analytical models and/or algorithms on the group record stored in the database 102 to calculate reports and insights for the multiple users. For example, the analyst computer 106 may execute the analytical models and/or algorithms to classify the information sources into categories that may be related to the type and origin of the data source. Then identify the correlations and relationships between collected information documents, and generate corresponding insights such as summary and health timeline of the multiple users for a pre-defined interval of time.

An analyst computer 106 may be a computing device comprising a processor and capable of performing the various processes and tasks described herein. Non-limiting examples of the analyst computer 106 may include laptops, desktops, servers, tablets, and smartphones. The analyst computer 106 may be coupled via one or more internal or external networks 110 to the database 104. The analyst computer 106 may produce an interactive user interface that allows the analyst to navigate the information displayed on the analyst computer 106, and may allow the analyst to generate, update, and monitor the information.

In operation, the analyst computer 106 may receive a group record comprising training data and healthcare data of multiple users from the server 102. The analyst computer 106 may apply analytical models and/or algorithms on the group record stored in the database 102 to calculate reports and insights for the multiple users. The analyst computer 106 may execute the analytical models and/or algorithms to classify various data sources into categories that may be related to the type and origin of the data source. The analyst computer 106 may then identify correlations and relationships between collected healthcare documents, and generate corresponding insights such as summary and health timeline of the multiple users for a pre-defined interval of time.

A database 104 may be hosted on a system 100, and is capable of storing training data. The database 104 may be in communication with a processor of a computing device of the system 100, where the processor is capable of executing the various commands of the system 100. In some embodiments, the database 104 may be part of the computer. In some embodiments, the database 104 may be a separate component in communication with the computer.

The system 100 may comprise one or more databases 104 that may be hosted on one or more computing devices, such as server computers, workstation computers, laptops, mobile devices, and tablets. The databases 104 may store data records comprising data fields that are associated with particular users, groups of users, etc. The server 102 may parse certain data fields of an inbound healthcare record of multiple users into distinct records or fields of data records of the database 104 in accordance with the standardized model, as indicated by the execution of the API. It should be appreciated that, although the system 100 shows only one database 104, however the system 100 may comprise any number of databases 104, hosted on any number computing devices, which may be any computing device comprising a non-transitory machine-readable storage medium and capable of performing the various tasks described herein.

Figure 2:
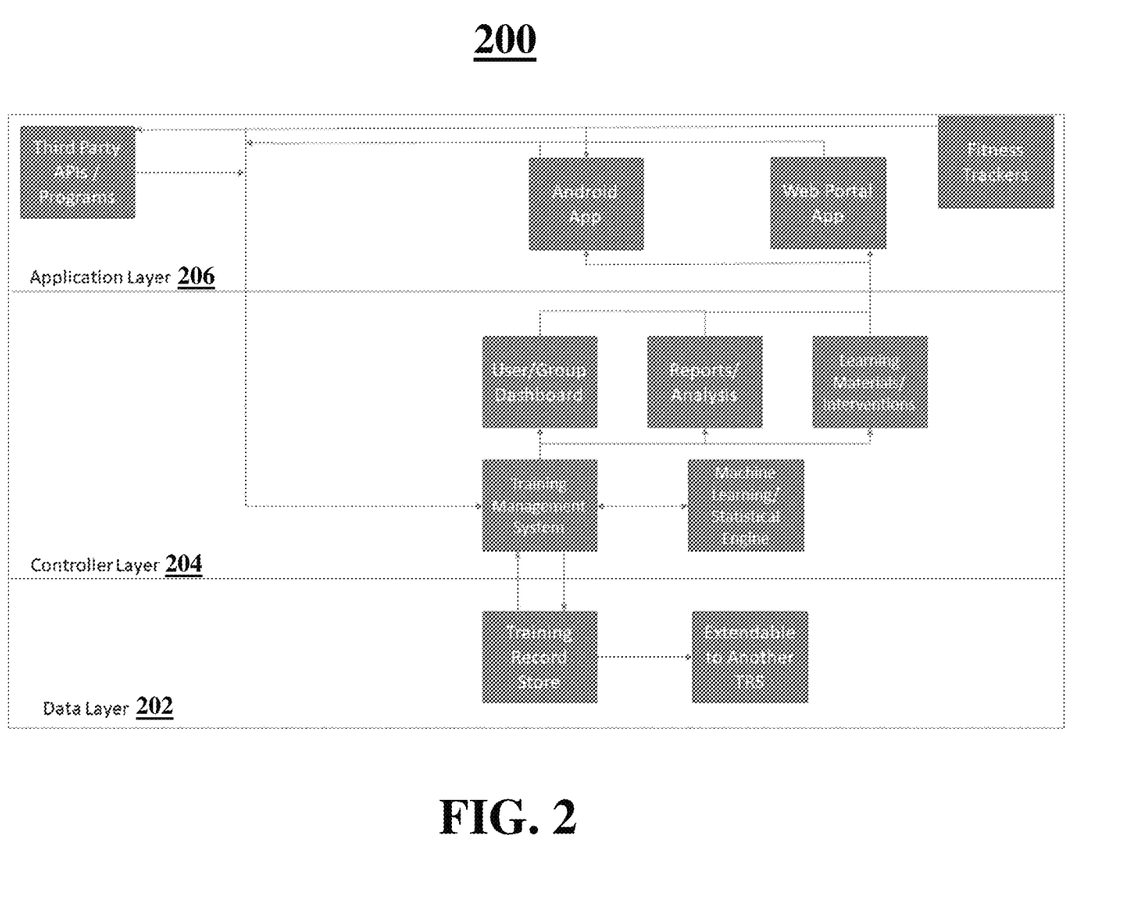
FIG. 2 illustrates architecture for processing fitness training data and healthcare data, according to an embodiment.

FIG. 2 illustrates a system architecture 200. The system architecture 200 utilizes an experience application programming interface (xAPI) to provide a blended training environment for users. The xAPI may track user's training data, standardize the tracked data, and aggregates the standardized data with data of other users to analyze and correlate experiences of the users. The xAPI has a three-layer architecture, which may include a data layer 202, a controller layer 204, and an application layer 206.

The data layer 202 is configured to store and retrieve user data from fitness tracking devices and/or healthcare applications. The data layer 202 may include a training record store (TRS). The TRS may include a server and a database that receives and processes web requests from various users. The TRS is defined in four parts using the xAPI. The four parts may include statements, activities, states, and agents. The xAPI may use xAPIs statements to create an interoperable data type, which may be sent to the TRS. The TRS may form a majority of a housing of data layer 202 that stores all of the data that the xAPI collects in an open standard and portable format. The TRS may contain definitions of activities and events during which the data will be collected from the fitness tracking devices. Also, the TRS may contain learning material and successful interference strategies to be applied automatically through a training management system (TMS). While the TRS is a database of statements, the TMS is a management system that controls the TRS.

The activity of the TRS may be used to define the activities to be taken by the users. The activities may make up the majority of the objects in the statements, and may include a list of training courses to be undertaken by the user. The TRS may track a state of completion the activity, which the user is actively working on one. This allows the TRS to keep track of activities that are worked on by the users over a period of time. The TRS may have a profile for an agent, which is a collection of identifiable information for the user. The information may include names, rank, personal email, or SSN of the user that may be needed to identify the user and collect data from different data sources.

The controller layer 204 is configured to manage users, manage groups of users, generate reports, validate data, and authenticate data. The controller layer 204 is made of the TMS. The TMS may function by responding to web requests to and from the TRS. The TMS may manage administrative tools, delivery of training material and interventions, as well as security and validation of users and data.

The TMS may control all data entering or leaving the TRS. The TMS may validate the users before connecting to the fitness tracking devices of the users. The TMS may further validate the data collected from the fitness tracking devices to make sure there are no invalid data figures. The TMS may enable user and group management operations. The TMS may further generate reports using the data, and provide analysis of the reports to user computing devices. The analysis of the reports may be in form of graphs displayed on a dashboard GUI of the user computing devices. Additionally, the TMS may provide access to various learning materials as well as strategies for the users tied to their specific training activities. The strategies may be presented in the form of additional reading material, smaller step goals to get a user better in line with the rest of the users in the group, or personal coaching. The additional reading material may include information associated with behavioral change strategies.

The application layer 206 may be made of android and web applications to read and collect data from fitness tracking devices, such as, mobile phones, watches, and wearable devices. The application layer 206 may be used to keep the users on track of their training program by providing reports to the users on their dashboards. The application layer 206 may also be used for entering and viewing the data by the users and the group of the users on the dashboards of their user computing devices.

Figure 3:
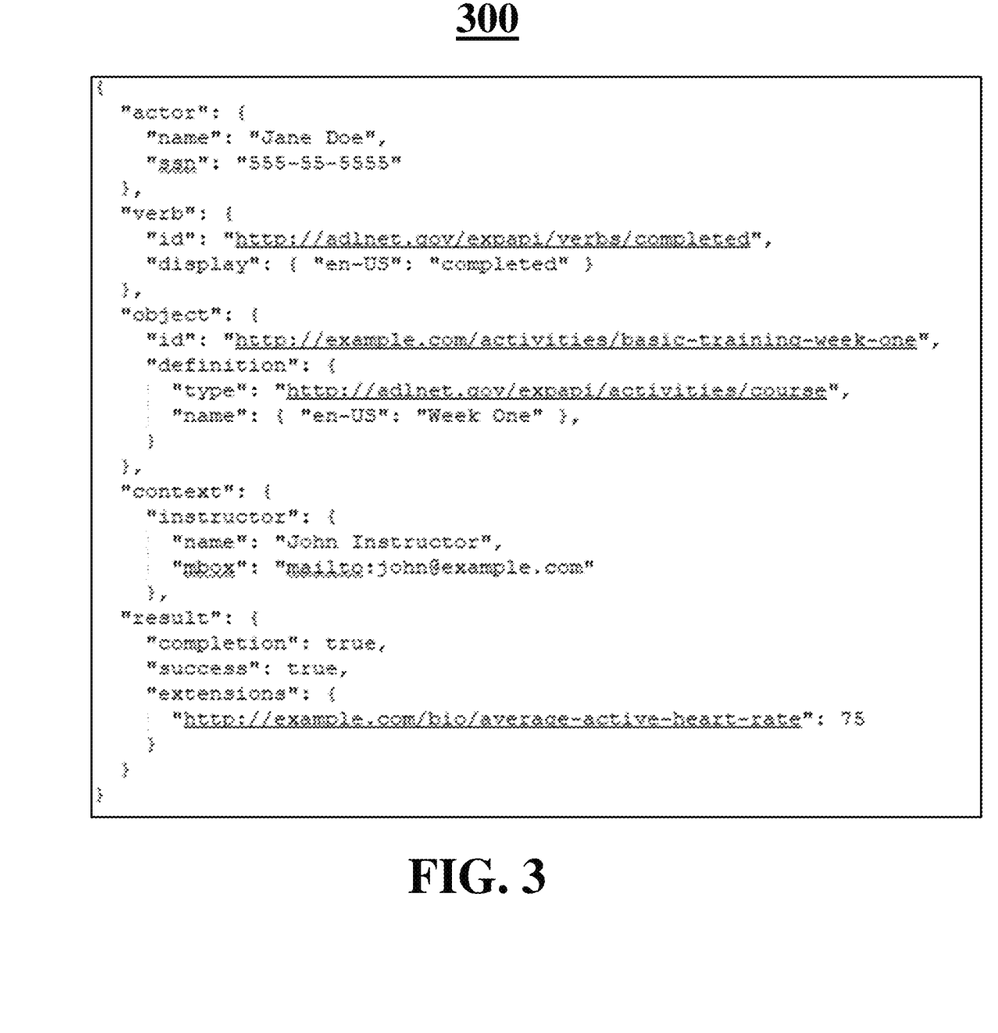
FIG. 3 illustrates an example for experience application programming interface (xAPI) statement, according to an embodiment.
Figure 4:
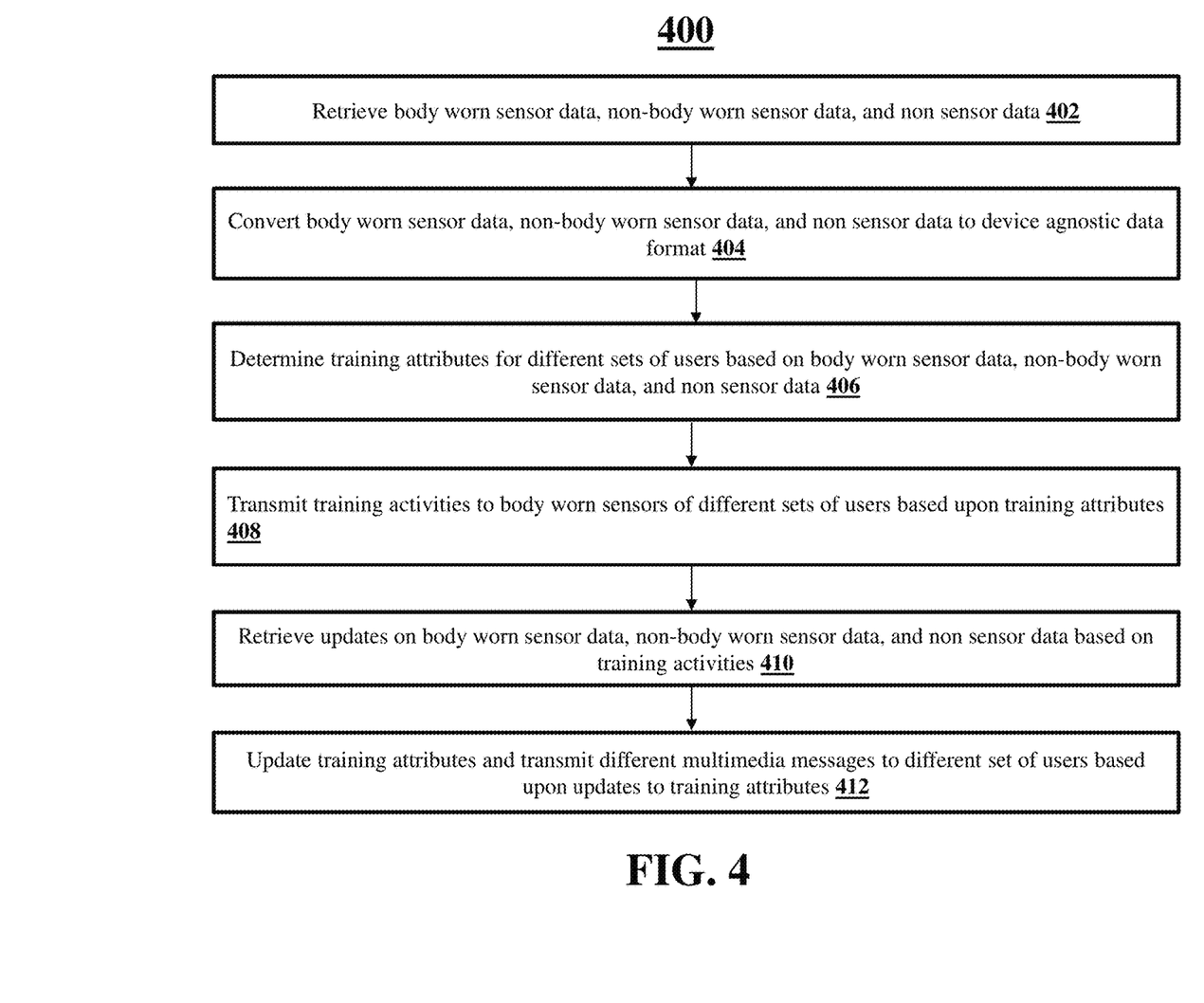
FIG. 4 illustrates a method for processing fitness training data and healthcare data, according to an embodiment.

FIG. 3 illustrates an example for an experience application programming interface (xAPI) statement 300. The core parts of the xAPI statement 300 are defined by an actor, verb, and object. A server computer may collect data from fitness tracking devices 108 as long as the data is in a form of the xAPI statement 300 and adheres to its definitions. The actor is a user or a group of users performing physical fitness activity. The objects are activities that the actor can perform. Results may be added to the xAPI statement 300 to show a measured outcome. Context may be added to make the xAPI statement 300 as detailed as needed. Extensions may be added to any part of the xAPI statement 300, which allow saving random data pairs that can be specific to the activity, the actor, or the application. The verb may describe what happened between the actor and the object, and there is a clear existing definition of what happened between the actor and the object. The xAPI statement 300 is a data format, and shows how to aggregate various types of the data in unique way to better capture user training experiences FIG. 4 shows a method for processing fitness training data and healthcare data, according to a method 400. The method 400 shown in FIG. 4 comprises execution steps 402, 404, 406, 408, 410, and 412. However, it should be appreciated that other embodiments may comprise additional or alternative execution steps, or may omit one or more steps altogether. It should also be appreciated that other embodiments may perform certain execution steps in a different order; steps may also be performed simultaneously or near-simultaneously with one another. In addition, the method 400 of the FIG. 4 is described as being executed by a single server computer in this embodiment. However, one having skill in the art will appreciate that, in some embodiments, steps may be executed by any number of server computers operating in a distributed computing environment. In some cases, the server computer executing one or more steps may be programmed to execute various other, unrelated features, where the server computer does not need to be operating strictly as described herein.

In a first step 402, a server computer may retrieve a first set of sensor data such as body-worn data from body-worn sensors of a plurality of users. The plurality of users may include a first set of users and a second set of users. The server computer may group the plurality of users into the first set of users and the second set of users. The grouping may be performed based on a predetermined criterion. The user devices of the first set of users may include the body-worn sensors of the first set of users. The user devices of the second set of users may include the body-worn sensors of the second set of users. The body-worn sensors of the first and the second set of users may include at least one of a smartwatch and a wrist worn fitness tracker.

The server computer may further retrieve a second set of sensor data such as non-body-worn sensor data associated with the plurality of users and collected from non-body-worn sensors of the plurality of users. The non-body-worn sensors may include an electronic target that records a corresponding user's shot in the field. The server computer may further retrieve a third set of non-sensor data such as non-sensor data entered manually by the plurality of users on user computing devices. The non-sensor data may include psychological data of the plurality of users.

In a next step 404, a server computer may convert the first set of sensor data, the second set of sensor data, and the third set of non-sensor data into a device agnostic data format. The device agnostic data format is experience application programming interface (xAPI). The xAPI is an e-learning software specification for learning technology that is able to collect data about the wide range of physical activity and other healthcare related experiences a user has online and offline. The xAPI captures the data in a consistent format about a user or group's activities. The system is able to securely communicate by capturing and sharing the stream of physical activities using xAPI.

In a next step 406, a server computer may determine a first set of training attributes of the first set of users and a second set of training attributes of the second set of users based upon the body-worn sensor data, the non-body-worn sensor data, and the non-sensor data. The first set of training attributes and the second set of training attributes may include a body weight, a heart rate, etc. The server computer may generate a training report based on the first set of training attributes and the second set of training attributes.

In a next step 408, a server computer may execute a neural network to generate a first and a second set of training activities based on the body-worn sensor data, the non-body-worn sensor data, and the non-sensor data. For instance, the server computer may execute the neural network to determine the first set of training activities based upon the first set of the training attributes, which are further determined based upon processing of the body-worn sensor data, the non-body-worn sensor data, and the non-sensor data. The server computer may determine the second set of training activities based upon the second set of the training attributes, which are further determined based upon processing of the body-worn sensor data, the non-body-worn sensor data, and the non-sensor data.

The server computer may transmit the first set of activities to the body-worn sensors of the first set of users based upon the first set of training attributes. The server computer may also transmit the second set of activities to the body-worn sensors of the second set of users based upon the second set of training attributes.

In a next step 410, a server computer may retrieve updates on the body-worn sensor data, the non-body-worn sensor data, and the non-sensor data based on training activities performed by the users. For instance, the server computer may retrieve a first set of updated sensor data from the body-worn sensors of the plurality of users based on the training activities performed by the users. The first set of updated sensor data includes the updated body-worn sensor data. The server computer may further receive a second set of updated sensor data associated with the plurality of users and collected from the non-body-worn sensors of the plurality of users based on the training activities performed by the users. The second set of updated sensor data includes the updated non-body-worn sensor data. The server computer may further receive a third set of updated non-sensor data entered manually by the plurality of users based on the training activities performed by the users. The third set of updated sensor data includes the updated non-sensor data. The updates to each set of data are based upon the first and the second set of activities.

In a next step 412, a server computer may determine a first set of updated training attributes of the first set of users based upon the updated body-worn sensor data, the updated non-body-worn sensor data, and the updated non-sensor data. The server computer may determine a second set of updated training attributes of the second set of users based upon the updated body-worn sensor data, the updated non-body-worn sensor data, and the updated non-sensor data.

The server computer may generate an updated training report based on the first set of updated training attributes and the second set of updated training attributes. The server computer may store the updated training report and the updated training attributes such as the first set of updated training attributes and the second set of updated training attributes in a database.

The server computer may generate multimedia messages based upon updates to the training attributes. The multimedia messages may include notes and memos for the users. The server computer may transmit the different multimedia messages to the different set of users. For instance, the server computer may transmit the different multimedia messages such as a first multimedia message and a second multimedia message to user computing devices of the first set of users and the second set of users based on the updated training attributes. In operation, a first multimedia message is displayed on a dashboard GUI of the first set of users based upon the first set of updated training attributes. The dashboard GUI is presented on a smartphone application or a on a web browser of the user computing devices of the first set of users. A second multimedia message is displayed on a dashboard GUI of the second set of users based upon the second set of updated training attributes. The dashboard GUI is presented on a smartphone application or a on a web browser of the user computing devices of the second set of users.

It should be understood that the aforementioned embodiments are not confined for training and other use cases should be included within the scope of this disclosure. Two illustrative examples are presented herein.

Example #1

A first set of users may have a first set of body-worn sensors and may be associated with a first set of non-body-worn sensors. The first set of body-worn sensors may be include smartwatches, a wrist worn fitness tracker, and/or any other body-worn sensors. The first set of non-body-worn sensors may include vehicular sensors such air bag sensors. Using the embodiments disclosed herein, a server may track sensor data from the first set of body-worn sensors and the first set of non-body-worn sensors for the first set of users. For the tracking, the server may convert the data received in various formats to a common format such as xAPI format. Using the tracked body-worn sensor data and non-body-worn sensor data, the server may generate one or more triggers to the sensors.

The first set of body-worn sensors may continuously track the behavior and/or vital signs (e.g., pulse/heart rate) of the first set of users and send the tracking data back to the server. Based on the tracked data, the server may determine whether a user is in motion from the tracking data received from a corresponding body-worn sensor. For example, the server may determine that the user is walking or running based upon accelerometer data and GPS data. For a user that is walking, the accelerometer data may show a slower pace and the GPS data may show a slower movement. For a user that is running, the accelerometer data may show a faster pace and the GPS data may show a faster movement. The server may also determine if a user is in an automobile. In this case, the accelerometer may show that the user does not have bodily movement consistent with walking or running but the GPS may show a movement of the user faster than a normal human running speed.

As described above, the server may also track the first set of non-body-worn sensors. The non-body-worn sensors may be sensors attached to a car such as an acceleration/deceleration sensors, braking sensors, and/or any other kind of sensors. The server may track the vehicular behavior based upon data stream received from the non-body-worn sensors and determine whether a vehicular behavior indicates a distress situation.

In exemplary scenario, the server may determine from the first set of non-body-worn sensors that there is a distress situation. The server may determine from an acceleration sensor, a rapid deceleration of the car and/or hard braking. The server may also determine that an airbag has inflated based upon data received from an airbag sensor.

Alternatively or additionally, the server may determine a distress situation based upon data received from a subset of the first set of body-worn sensors. The server may determine that a corresponding subset of users is traveling in a car based upon acceleration data and GPS data received from the subset of the first set of body-worn sensors. For example, the server may determine that the pulse rate of corresponding subset of the first set of users may have spiked roughly at the same time. The spiked in the pulse rate may indicate a distress situation as perceived by the subset of the first set of users. The server may time-align the data received from the body-worn sensors and non-body-worn sensors to make the determination of the distress situation.

In response to determining the distress situation, the server may trigger one or more response operations. For example, the server may determine that a first subset of a first set of users is in a distress situation and alert a second subset of the first set of users that the first subset of users are in a distress situation. The first set of users may be members of the same family and when some family members experience a distress situation, the server may automatically alert other family members who are not in a distress situation. The server may also alert authorities about the distress situation.

Example #2

A second set of users may be a member of a same family and may be wearing a second set of body-worn sensors. The family house may be associated with a second set of non-body-worn sensors. For instance, a non-body-worn sensor may be a smart doorbell that generates sensor data when someone presses or approaches the smart doorbell. Other examples of the non-body-worn sensors may include door/window sensors, which indicate if a corresponding door/window is open or is closed.

The server may determine a distress situation based upon sensor data received from at least one of the second set of body-worn sensors and at least one of the non-body-worn sensors. For instance, when the server detects that a window is opened based upon the data received from the corresponding non-body-worn sensors. The server may track the behavior of the users who are inside the house (e.g., determined based upon the data received from the GPS sensor of a smartwatch) in response to the opening of the window. If the server determines from the body-worn sensors that there is an elevation in pulse rate of the users in the house and movement consistent with startling, the server may determine that the users in the house are distressed and alert other family members. In addition, the server may alert the authorities.

Figure 5:
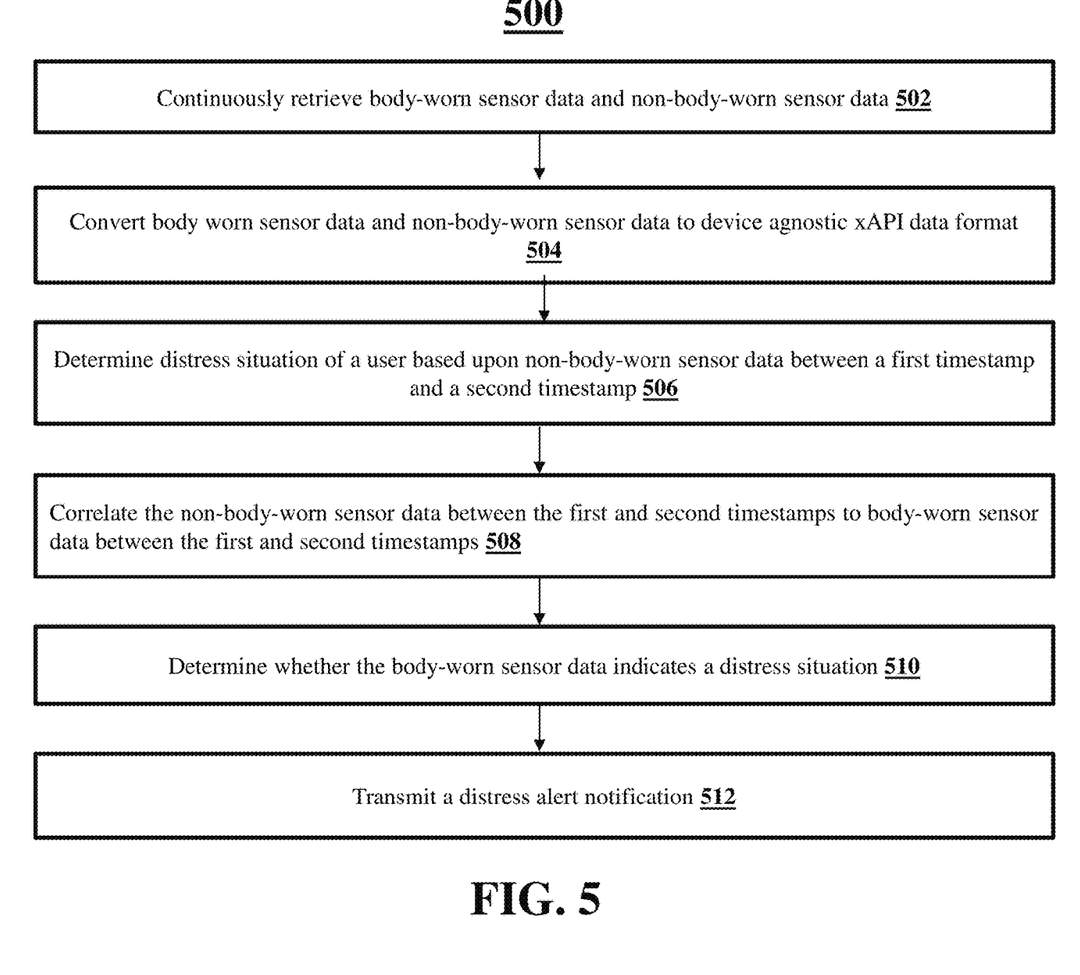
FIG. 5 illustrates a method of triggering an alert based on sensor data, according to an embodiment.

FIG. 5 shows a flow diagram of an illustrative method 500 of generating alerts based upon sensor data, according to an embodiment. It should be understood the steps described herein are merely illustrative and additional, alternative, and fewer number of steps should be considered within the scope of this disclosure. It should further be understood that although multiple computing systems may execute one or more steps of the method 500, the following details, for brevity, a single computer executing the steps.

The method 500 may begin at step 502, where the computer may continuously receive (or, alternatively, retrieve) body-worn sensor data associated with a plurality of users. The body-worn sensor data may be from body-worn devices such as smartwatches and fitness trackers. The non-body-worn sensor data may be sensor data from sensors in the cars of the plurality of users and home sensor data from homes of the plurality of users. These sensors may transmit the data to the computer in a real-time basis or in an intermittent basis based upon the connectivity in between.

In a next step 504, the computer may convert the body-worn sensor data and the non-body-worn sensor data to a device agnostic xAPI data format. The xAPI format may allow the computer to correlate data collected from various incompatible sensors. For example, xAPI may allow the computer to compare the timestamps of data collected by a smartwatch and the data collected by a home-sensor such the computer may perform data operations in the data collected in the same timeframe.

In a next step 506, the computer may determine a distress situation of the user based non-body-worn sensor data retrieved between a first timestamp and a second timestamp. For example, the non-body-worn sensor data may be an acceleration sensor inside a car. The computer may determine that acceleration data received from the acceleration sensor within a time window (as indicated by the first and second timestamps) indicate a rapid and sudden deceleration of the car. Such rapid deceleration may indicate an accident. Alternatively or additionally, the computer may determine that an airbag in the car has inflated through data from an airbag sensor, which also may indicate a distress situation. It should be understood that these sensors and the corresponding distress situation determination are merely illustrative and other sensors and distress situation determination should also be considered within the scope of this disclosure.

In a next step 508, the computer may correlate the non-body-worn sensor data between the first and second timestamps to body-worn sensor data between the first and second timestamps. For example, using the first and second timestamps, the computer may query and retrieve body-worn sensor data of the user.

In a next step 510, the computer may determine whether the body-worn sensor data indicates a distress situation. For example, the computer may determine whether the heart rate of the user as spiked. A spiked heart rate may indicate distress. As another example, the computer may determine whether the user has a sudden movement based upon accelerometer measurements. The computer may use the body-worn sensor data to confirm a distress situation that was determined based upon the non-body-worn sensor data.

In a next step 512, the computer may trigger a distress alert notification. For example, the computer may send a distress to a second user who is related to the first user. The distress may in the form of a text message, e-mail, automated telephone call, and/or any other type of message. The computer may also provide the distress alert notification to authorities (e.g., law enforcement) as well.

Figure 6:
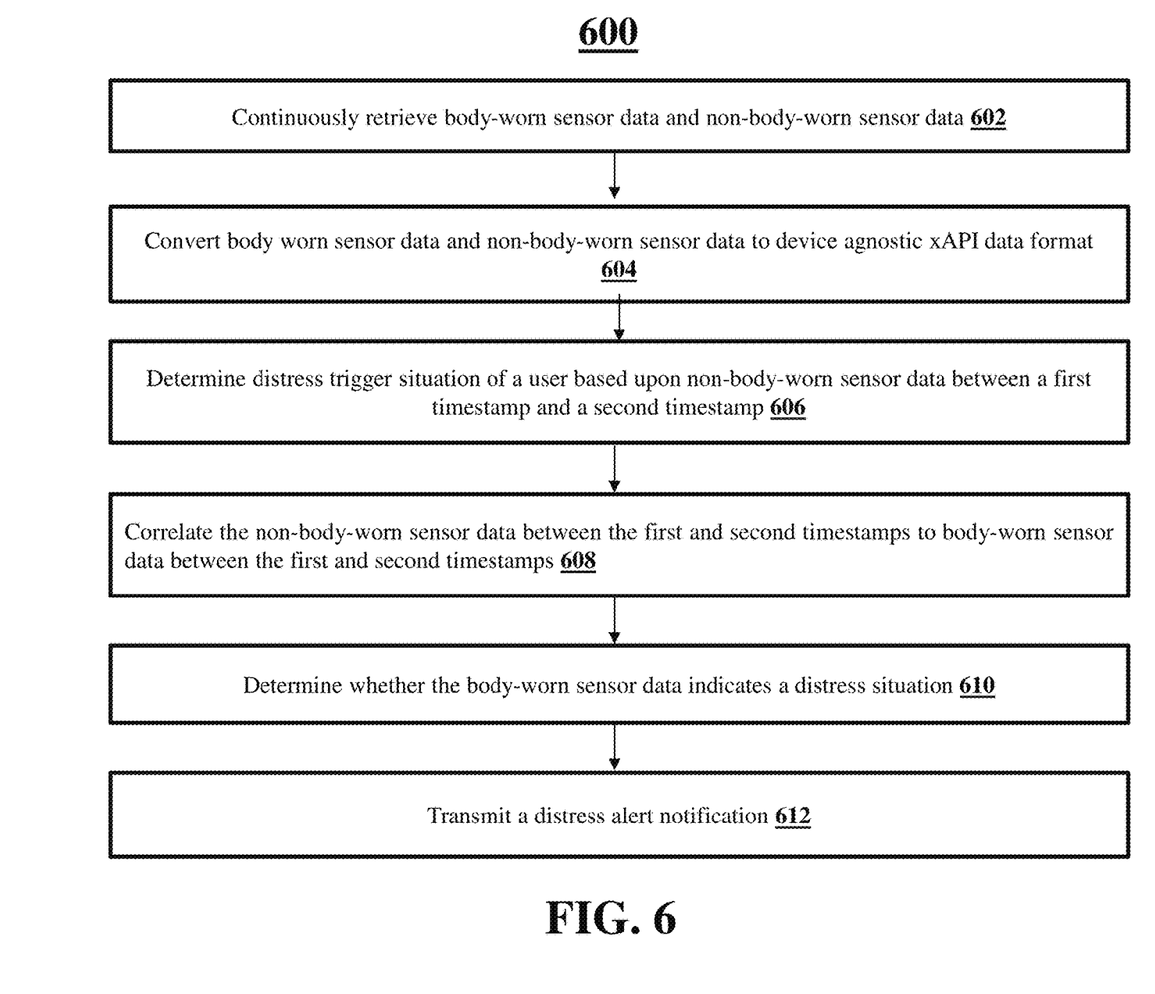
FIG. 6 illustrates a method of triggering an alert based on sensor data, according to an embodiment.

FIG. 6 shows a flow diagram of an illustrative method 600 of generating alerts based upon sensor data, according to an embodiment. It should be understood the steps described herein are merely illustrative and additional, alternative, and fewer number of steps should be considered within the scope of this disclosure. It should further be understood that although multiple computing systems may execute one or more steps of the method 600, the following details, for brevity, a single computer executing the steps.

The method 600 may begin at step 602, where the computer may continuously receive body-worn sensor data associated with a plurality of users. The body-worn sensor data may be from body-worn devices such as smartwatches and fitness trackers. The non-body-worn sensor data may be sensor data from sensors in the cars of the plurality of users and home sensor data from homes of the plurality of users.

These sensors may transmit the data to the computer in a real-time basis or in an intermittent basis based upon the connectivity in between.

In a next step 604, the computer may convert the body-worn sensor data and the non-body-worn sensor data to a device agnostic xAPI data format. The xAPI format may allow the computer to correlate data collected from various incompatible sensors. For example, xAPI may allow the computer to compare the timestamps of data collected by a smartwatch and the data collected by a home-sensor such the computer may perform data operations in the data collected in the same timeframe.

In a next step 606, the computer may determine a distress trigger situation of the user based non-body-worn sensor data retrieved between a first timestamp and a second timestamp. For instance, a non-body-worn sensor may be a home sensor, e.g., a window sensor indicating a whether a corresponding window is open or closed. When the state of the window changes from closed to opened, that may be a distress situation of a home invasion or break-in.

In a next step 608, the computer may correlate the non-body-worn sensor data between the first and second timestamps to body-worn sensor data between the first and second timestamps. For example, using the first and second timestamps, the computer may query and retrieve body-worn sensor data of the user.

In a next step 610, the computer may determine whether the body-worn sensor data indicates a distress situation. For example, the computer may determine whether the heart rate of the user as spiked. A spiked heart rate may indicate distress. As another example, the computer may determine whether the user has a sudden movement based upon accelerometer measurements. The computer may use the body-worn sensor data to confirm whether the distress trigger situation was real or just a false alarm (e.g., homeowner opening a window).

In a next step 612, the computer may trigger a distress alert notification. For example, the computer may send a distress to a second user who is related to the first user. The distress may in the form of a text message, e-mail, automated telephone call, and/or any other type of message. The computer may also provide the distress alert notification to authorities (e.g., law enforcement) as well.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the generic principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer-implemented method comprising:
   continuously receiving, by a computer, body-worn sensor data from body-worn sensors of a plurality of users and non-body-worn sensor data associated with the plurality of users and collected from non-body-worn sensors;
   converting, by the computer, the body-worn sensor data and the non-body-worn sensor data into device-agnostic experience application programming interface (xAPI) data format;
   determining, by the computer, a distress situation of a user of the plurality of users based upon non-body-worn sensor data retrieved between a first timestamp and a second timestamp;
   correlating, by the computer, the non-body-worn sensor data between the first timestamp and the second timestamp to body-worn sensor data of the user between the first timestamp and the second timestamp;
   determining, by the computer and based on correlating the non-body-worn data to the body-worn sensor data, whether the body-worn sensor data of the user between the first timestamp and the second timestamp indicates the distress situation; and
   in response to the computer determining the distress situation from the non-body sensor data and the body-worn sensor data, transmitting, by the computer, a distress alert notification to a second user of the plurality of users.

2. The computer-implemented method of claim 1, wherein the body-worn sensors of the plurality of users include at least one of a smartwatch and a wrist worn fitness tracker.

3. The computer-implemented method of claim 1, wherein the non-body-worn sensors include at least one of a sensor in a car and a sensor in a home.

4. The computer-implemented method of claim 1, wherein the non-body-worn sensor data is a car acceleration sensor data of a car associated with the user and wherein determining distress situation of the user based upon the non-body-worn sensor data retrieved between the first timestamp and the second timestamp comprises:
   determining, by the computer, a rapid deceleration of the car between the first timestamp and the second timestamp based upon the car acceleration data.

5. The computer-implemented method of claim 1, wherein the non-body-worn sensor data is an air bag sensor data of a car associated with the user and wherein the determining stress situation of the user based upon the non-body-worn sensor data retrieved between the first timestamp and the second timestamp comprises:
   determining, by the computer, an airbag inflation in the car between the first timestamp and the second timestamp based upon the air bag sensor data.

6. The computer-implemented method of claim 1, wherein the body-worn sensor data is heart rate data and wherein determining whether the body-worn sensor data of the user between the first timestamp and the second timestamp indicates a distress situation comprises:
   determining, by the computer, a spike in the heart rate between the first timestamp and the second timestamp based upon the heart rate data.

7. The computer-implemented method of claim 1, wherein the body-worn sensor data is accelerometer data and wherein determining whether the body-worn sensor data of the user between the first timestamp and the second timestamp indicates a distress situation comprises:
   determining, by the computer, a sudden movement of the user between the first timestamp and the second timestamp based upon the accelerometer data.

8. A computer-implemented method comprising:
   continuously receiving, by a computer, body-worn sensor data from body-worn sensors of a plurality of users, and non-body-worn sensor data associated with the plurality of users and collected from non-body-worn sensors;
   converting, by the computer, the body-worn sensor data and the non-body-worn sensor data into device-agnostic experience application programming interface (xAPI) data format;
   determining, by the computer, a distress trigger situation of a user of the plurality of users based upon non-body-worn sensor data retrieved between a first timestamp and a second timestamp;
   correlating, by the computer, the non-body-worn sensor data between the first timestamp and the second timestamp to the body-worn sensor data of the user between the first timestamp and the second timestamp;
   determining, by the computer and based on correlating the non-body-worn data to the body-worn sensor data, whether the body-worn sensor data of the user between the first timestamp and the second timestamp indicates a distress situation; and
   in response to the computer determining the distress situation based upon the body-worn sensor data, transmitting, by the computer, a distress alert notification to a second user of the plurality of users.

9. The computer-implemented method of claim 8, wherein the body-worn sensors of the plurality of users include at least one of a smartwatch and a wrist worn fitness tracker.

10. The computer-implemented method of claim 8, wherein the non-body-worn sensors include at least one of a sensor in a car and a sensor in a home.

11. The computer-implemented method of claim 8, wherein the non-body-worn sensor data is a home sensor data of a home associated with the user and wherein determining distress trigger situation of the user based upon the non-body-worn sensor data retrieved between the first timestamp and the second timestamp comprises:
   determining, by the computer, an opening of a window between the first timestamp and the second timestamp based on the home sensor data.

12. The computer-implemented method of claim 8, wherein the body-worn sensor data is heart rate data and wherein determining whether the body-worn sensor data of the user between the first timestamp and the second timestamp indicates a distress situation comprises:
   determining, by the computer, a spike in the heart rate between the first timestamp and the second timestamp based on the heart rate data.

13. The computer-implemented method of claim 8, wherein the body-worn sensor data is accelerometer data and wherein determining whether the body-worn sensor data of the user between the first timestamp and the second timestamp indicates a distress situation comprises:
  determining, by the computer, a sudden movement of the user between the first timestamp and the second timestamp based on the accelerometer data.

14. A system comprising:
  a non-transitory storage medium storing a plurality of computer program instructions;
  a processor electrically coupled to the non-transitory storage medium and configured to execute the plurality of computer program instructions to:
    continuously receive body-worn sensor data from body-worn sensors of a plurality of users, and non-body-worn sensor data associated with the plurality of users and collected from non-body-worn sensors;
    convert the body-worn sensor data and the non-body-worn sensor data into device-agnostic experience application programming interface (xAPI) data format;
    determine a distress situation of a user of the plurality of users based upon non-body-worn sensor data retrieved between a first timestamp and a second timestamp;
    correlate the non-body-worn sensor data between the first timestamp and the second timestamp to the body-worn sensor data of the user between the first timestamp and the second timestamp;
    determine, based on correlating the non-body-worn data to the body-worn sensor data, whether the body-worn sensor data of the user between the first timestamp and the second timestamp indicates distress situation; and
    in response to the processor determining the distress situation from non-body sensor data and the body-worn sensor data, transmit a distress alert notification to a second user of the plurality of users.

15. The system of claim 14, wherein the body-worn sensors of the plurality of users include at least one of a smartwatch and a wrist worn fitness tracker.

16. The system of claim 14, wherein the non-body-worn sensors include at least one of a sensor in a car and a sensor in a home.

17. The system of claim 14, wherein the non-body-worn sensor data is a car acceleration sensor data of a car associated with the user and wherein to determine distress situation of the user based upon the non-body-worn sensor data retrieved between the first timestamp and the second timestamp, the processor is configured to further execute the plurality of computer instructions to:
  determine a rapid deceleration of the car between the first timestamp and the second timestamp based on the car acceleration data.

18. The system of claim 14, wherein the non-body-worn sensor data is an air bag sensor data of a car associated with the user and wherein to determine the distress situation of the user based upon the non-body-worn sensor data retrieved between the first timestamp and the second timestamp, the processor is configured to further execute the plurality of computer program instructions to:
  determine an airbag inflation in the car between the first timestamp and the second timestamp based on the air bag sensor data.

19. The system of claim 14, wherein the body-worn sensor data is heart rate data and wherein to determine whether the body-worn sensor data of the user between the first timestamp and the second timestamp indicates a distress situation, the processor is configured to further execute the plurality of computer program instructions to:
  determine a spike in the heart rate between the first timestamp and the second timestamp based on the heart rate data.

20. The system of claim 14, wherein the body-worn sensor data is accelerometer data and wherein to determine whether the body-worn sensor data of the user between the first timestamp and the second timestamp indicates a distress situation, the computer is configured to further execute the plurality of computer program instructions to:
  determine a sudden movement of the user between the first timestamp and the second timestamp based on the accelerometer data.

* * * * *